United States Patent [19]
Jacq et al.

[11] Patent Number: 5,644,091
[45] Date of Patent: Jul. 1, 1997

[54] MATERIAL SAMPLING METHOD AND DEVICE

[75] Inventors: Patrick H. Jacq, Montigny Le Bretonneux; Daniel M. Kerlau, Chatenay-Malabry; Patrice B. Roux, Paris; Claude A. Gineste, Villefranche de Panat, all of France

[73] Assignee: Compagnie Generale des Matieres Nucleaires, Velizy-Villacoublay, France

[21] Appl. No.: 491,950

[22] PCT Filed: Jan. 26, 1994

[86] PCT No.: PCT/FR94/00092

§ 371 Date: Jul. 18, 1995

§ 102(e) Date: Jul. 18, 1995

[87] PCT Pub. No.: WO94/17386

PCT Pub. Date: Aug. 4, 1994

[30] Foreign Application Priority Data

Jan. 26, 1993 [FR] France ................................ 93 00717

[51] Int. Cl.[6] ..................................................... G01N 1/08
[52] U.S. Cl. .......................................................... 73/864.44
[58] Field of Search ............................. 73/864.44, 864.45, 73/864.62, 864.63; 175/20, 58

[56] References Cited

U.S. PATENT DOCUMENTS 2,298,350  10/1942  Davidson .
4,376,392  3/1983   Beitel .
4,887,413  12/1989  Tuckey, Jr. ............................ 73/864.44

FOREIGN PATENT DOCUMENTS

| 1419025 | 10/1965 | France | 73/864.44 |
|---|---|---|---|
| 2 088 863 | 1/1972 | France . | |
| 2 260 792 | 2/1974 | France . | |
| 2 279 090 | 7/1974 | France . | |
| 2 632 726 | 6/1988 | France . | |
| 2435884 | 2/1976 | Germany | 175/20 |
| 61-175543 | 8/1986 | Japan . | |

OTHER PUBLICATIONS

International Search Report for corresponding International Application No. PCT/FR 94/00092, dated May 4, 1994.

Patent Abstracts of Japan; vol. 10, No. 250, p. 491, Aug. 28, 1986.

*Primary Examiner*—R. Raevis
*Attorney, Agent, or Firm*—Cohen, Pontani, Lieberman, Pavane

[57] ABSTRACT

The present invention relates to a device and to a method for taking samples of a material such as a liquid, a viscous fluid, or a friable solid. Said device comprises a hollow "sampling" cylinder (10) defining an open cavity, said cavity co-operating with vent-forming means (34) and including inflatable shutter means (20) shaped so that, after said cavity has been filled with said material, they hold said material inside said cavity.

18 Claims, 3 Drawing Sheets

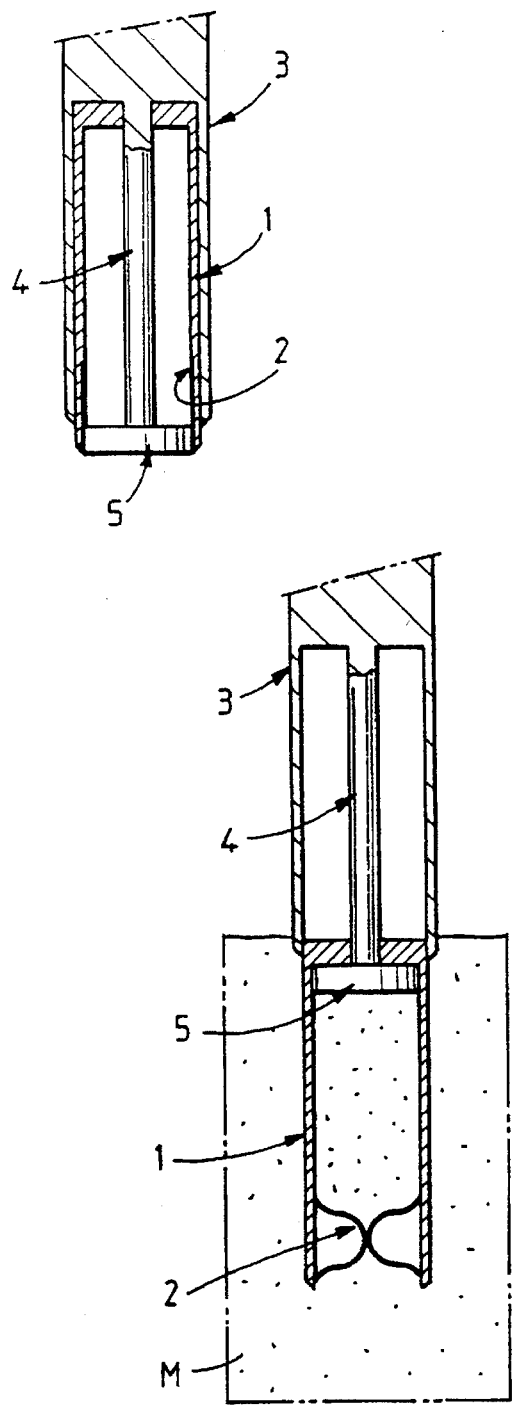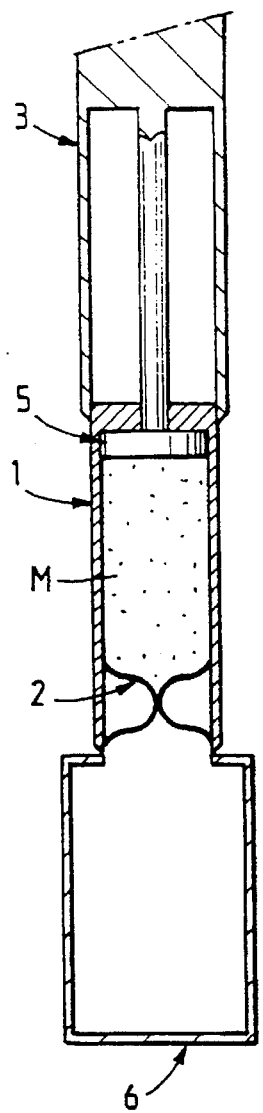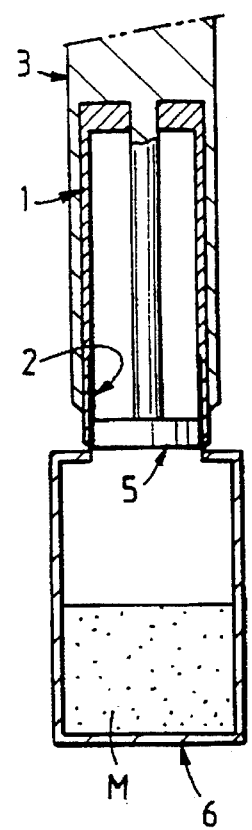

MATERIAL SAMPLING METHOD AND DEVICE

The present invention relates to a device for sampling a material and to the method of taking samples of said material by using said device.

Said device and method of the invention are particularly suitable for taking samples of a material such as a liquid—solution or suspension—a viscous fluid—sludges, for example—or a friable solid—a solid having very low hardness: sand or a hard solid that has previously been crushed—.

At present:

solid samples are taken by using core-drilling equipment. Such tools mainly comprise a hollow tube mounted at the end of a string of rods and having a sharp bottom edge;

to take samples of sludges, a core-drilling equipment is used initially to drill a sampling well, after which a pump is used to take the sample contained in the well;

for sampling liquids, it is general to use syringes or pumps.

The present invention proposes an original device which is nevertheless unsuitable for taking samples of a material that is hard, as will easily be seen by the person skilled in the art and reading the text below. Said device is particularly suitable for taking samples of sludges.

The device of the invention comprises a hollow "sampling cylinder" or "sample-taking" cylinder defining an open cavity, said cavity co-operating with vent-forming means and also including inflatable shutter means shaped, after said cavity has been filled with said material, to ensure that said material is held inside said cavity.

Once inserted into the mass of material to be sampled, said hollow cylinder is intended to fill, at least in part, with said material. To this end, at least one opening is provided, and the open cavity defined in this way co-operates with vent-forming means enabling the air (or possibly some other gas initially present in said cavity) to be expelled by the material as the cavity fills with said material.

Said vent may be formed directly through one of the walls of the open cavity. It may also be provided in another part of a device that is more complex: said device including both the sampling cylinder and means for putting the inside of said cylinder (the sampling cavity) into communication with said vent.

The sampling cavity also includes inflatable shutter means suitable for shutting its opening(s) after it has filled, and for holding the sampled material that has been trapped in this way inside the cavity. Said means are retractable during positioning of the sampling device and while it is filling. They are connected to a device capable of applying pressure thereto in order to shut the opening(s) of the sampling cylinder and in order to apply suction thereto to open said opening(s). Said inflatable shutter means advantageously comprise a rubber membrane that has been thoroughly checked for strength and constant thickness. Said membrane must be capable of withstanding internal pressure suitable for closing the cavity in sealed manner while it contains the sample that has been taken.

The sampling cavity of the device of the invention is described above using the term "hollow cylinder". This term is not limiting in any way. The person skilled in the art will easily understand that the teaching of the present invention is transposable to other embodiments and in particular to cavities that are hemispherical, bell-shaped, . . . . Advantageously, the cavity of the sampling device of the invention is a circular cylinder.

Said sampling device of the invention may consist in the means described above: a sampling cylinder with one or more filling openings, a vent, and inflatable shutter means for the said opening(s) and connected to a source for feeding gas under pressure.

Advantageously, said means, which are essential, are associated with other means.

Thus, the device of the invention advantageously includes, in addition to the essential means described above, means for providing guided displacement of the sampling cylinder between a position in which the opening(s) of said cylinder is/are outside the material to be sampled, and a "sampling" position in which the opening(s) is/are in said material, and means for stopping said displacement and positioning said cylinder in said sampling position.

For these purposes of guiding and positioning in the sampling position, it is possible to design numerous devices and in particular to use co-operation between at least one stud on the outside face of the sampling cylinder and a groove formed in a part external to said cylinder. All such devices form an integral portion of the present invention.

The displacement and the positioning of said sampling cylinder while empty, and also recovery thereof when full can be operations that are entirely manual, or else various mechanical means may be involved.

The invention is described below in greater detail with reference to one of its preferred variants, in which variants:

said sampling cylinder is open at its bottom;

said inflatable shutter means are positioned in the vicinity of said bottom; and said sampling cylinder is mounted to be displaceable in vertical downward translation inside another cylinder referred to as the "outer" cylinder which is likewise open at the bottom and which includes means for stopping and positioning said sampling cylinder in a low, sampling position; said outer cylinder serving to guide said sampling cylinder during such movement in translation.

Said sampling cylinder and said outer cylinder are organized for and/or include vent-forming means enabling the device to operate properly.

Guidance of said sampling cylinder inside said outer cylinder can be provided in different variants using known means. In particular, over at least a portion of their height, the outer face of said sampling cylinder and the inner face of said outer cylinder may include means designed to co-operate and prevent any rotation of one of said cylinders relative to the other. Said means may be of the type comprising a longitudinal groove and a stud.

To improve guidance of said sampling cylinder inside said outer cylinder, it is also advantageously possible to provide at least one rod that is secured at its top end to said outer cylinder and at its bottom end to a stationary piston. Said stationary piston constitutes stop and positioning means for said sampling cylinder in its low, sampling position, and is also advantageously of a size relative to the bottom of said outer cylinder suitable, during downward translation movement of said sampling cylinder to provide sealing for the pressure chamber thus defined by said outer cylinder and said stationary piston, in which pressure chamber said sampling cylinder moves in downward translation.

A plurality of rods may be provided. Advantageously, a single, central rod is provided on the common axis of said sampling and outer cylinders.

The sampling cylinder is thus mounted inside a pressure chamber to be displaceable in translation inside the outer cylinder whose bottom is "shut" by the stationary piston.

Naturally, said downward translation movement of the sampling cylinder is possible only if the inside of said sampling cavity or cylinder cooperates with vent-forming means. Such a vent may be provided in the top wall of said sampling cylinder, thereby enabling excess pressure in the outer cylinder to be exhausted.

In another variant, which is preferred, the sampling cavity communicates via the rod with the outside. In this variant, said rod is hollow, including at least one orifice in its bottom portion in the vicinity of the stationary piston and opening out to the inside of the sampling cylinder, and connected at its top end to a vent level with the top portion or head of the outer cylinder. Thus, as the empty sampling cylinder moves downwards, the gas it initially contains is exhausted via said hollow rod. Said cylinder is stopped in its sampling position by the stationary piston.

Advantageously, said stationary piston includes an electrical contact on its top face for the purpose of indicating that the sampling cylinder is in its low, sampling position.

In a preferred variant, said stationary piston is organized as follows: it comprises two portions that are united and a gasket that is held horizontal between them. Said gasket has two functions. Firstly it provides sealing between the sampling cavity and the pressure chamber during the downward translation movement of the sampling cylinder, and secondly it acts during the downward movement of the outer cylinder over said sampling cylinder. During said downward movement of the outer cylinder it acts as a scraper, thereby cleaning the inside walls of the sampling cylinder. When the device of the invention is used for taking a sample of material, it is necessary to perform this step of moving the said outer cylinder downwards over the inner, sampling cylinder.

Such use comprises the following steps:

the sampling cylinder is initially engaged inside the outer cylinder;

said sampling cylinder is lowered until it comes into abutment against the stationary piston, for insertion into the material from which a sample is to be taken;

said cylinder is filled with said material;

said cylinder is then shut at its bottom end by inflating the inflatable shutter means; the sample of material that has been taken is thus trapped inside the sampling cylinder in its low position;

said cylinder is then extracted from said material;

said cylinder, still in its low position in abutment against the stationary piston, is then emptied of the material it contains by deflating said shutter means; the cylinder is then empty and in its low position; and the said outer cylinder is then lowered over said sampling cylinder and said gasket performs its scraper function. The sampling cylinder is then again engaged inside said outer cylinder.

Taking a sample constitutes one cycle.

To lower the sampling cylinder into its low, sampling position provision is made to inject a fluid under pressure into the top portion or head of the outer cylinder. Said fluid is intended to fill the pressure chamber. To this end, the top portion of said outer cylinder includes appropriate injection means. Said top portion must also include means for exhausting said fluid while the outer cylinder is moving down over said sampling cylinder in its low position. Advantageously, said top portion of the outer cylinder includes an opening to which a coupling can be fitted, which coupling is alternately connected to a source for feeding fluid under pressure, and left open to the outside to constitute a vent. The fluid under pressure that is used advantageously comprises a gas under pressure, such as compressed air.

To inflate the shutter means of the sampling cavity, it is also necessary to provide appropriate means. Said inflatable shutter means advantageously comprise a membrane able to generate a ring-shaped tube. As mentioned above, said membrane must have elasticity and strength suitable for performing its function. In order to shut the bottom of a circular cylinder, said membrane, when inflated, takes up the shape of an annular and peripheral inner tube.

The means required for inflating and deflating said inflatable shutter means advantageously consist in connection means connecting said inflatable shutter means to a source for feeding a fluid under pressure (for inflation) and enabling said fluid to travel in the opposite direction (for deflation). Said connection means may consist, for example, in a capillary tube and a hose; said capillary tube is situated in the body of the sampling cylinder and connects said membrane to said hose which is situated in the head of said outer cylinder; said hose is connected to the source for feeding fluid under pressure (inflation fluid). Naturally, the length of said hose is adapted to the stroke of the sampling cylinder (between its high position inside the outer cylinder and its low or sampling position). The fluid under pressure that is used advantageously consists in a gas under pressure, such as compressed air.

It is emphasized at this point that in the device of the invention the operation of lowering the sampling cylinder to place it within the material, and the operation of inflating the inflatable shutter means are totally independent. These two operations are implemented with different means.

Advantageously, they make use of a gas such as compressed air. It is preferable to use a gas rather than a liquid. The device is thus made more independent and easier to manipulate.

In general, the device of the invention is very flexible in use. It is entirely suitable for taking contaminated and/or radioactive samples in an active cell.

While the outer cylinder is moving down over the sampling cylinder that has been emptied of its contents, the stationary piston scrapes the inside walls of said sampling cylinder and thus performs a certain amount of cleaning. It will readily be understood that said cleaning is made more effective if the piston is provided with a gasket, as mentioned above. Nevertheless, in order to improve said cleaning, it is possible to provide for a cleaning fluid to be used, which fluid is advantageously conveyed via the central rod. As mentioned above, said rod is empty and provides communication between the inside of the sampling cavity and the outside via a vent which is provided on the top portion or head of the outer cylinder. It is possible to make provision on said vent for receiving a cleaning liquid injector device to inject said liquid while the sampling cylinder is in its low position, and is empty, and while the outer cylinder is moving downwards. Said liquid travels down along the hollow rod, passes through the orifice(s) provided in the bottom of said rod, and flows into an annular gap advantageously formed in the top portion of the sampling cylinder. Said liquid can be removed from the bottom because of the elasticity of the gasket held between the two portions of the piston.

Said gasket advantageously provides sealing while the sampling cylinder is being moved in downward translation, but does not provide sealing under the pressure of the cleaning liquid while the outer cylinder is being moved in downward translation.

It is mentioned above that the outer cylinder moves down over the empty sampling cylinder. Nevertheless, it is perfectly possible for said outer cylinder to begin its downwards movement and to continue it while said sampling cylinder is emptying under gravity. The downwards movement of said outer cylinder may assist in emptying out the sample through the bottom.

The device of the invention as described above includes a sampling cylinder whose bottom end is advantageously given a profile that is optimized for the purpose of facilitating penetration into the material from which a sample is to be taken. Said end is advantageously chamfered.

The present invention also provides a method of taking samples of a material such as a liquid, a viscous fluid, or a friable solid; the method is implemented using a device as described above. Said method comprises in particular:

inserting the sampling cylinder of the invention into said material under drive from a fluid injected into the pressure chamber defined by the outer cylinder and the stationary piston, and until said sampling cylinder comes into abutment against the piston;

waiting for sufficient time to enable said material to fill said sampling cylinder;

inflating the inflatable shutter means with a fluid under pressure in order to hold said material trapped in said sampling cylinder;

extracting from said material said sampling cylinder containing said sample of material;

deflating said inflatable shutter means to recover said sample of material; and lowering the outer cylinder over said sampling cylinder.

Said sampled material is recovered when it flows out under gravity. In the preferred variant of the invention, said material may also be caused to flow within the device under drive from the stationary piston by downward movement of the outer cylinder over the inner cylinder in its low position.

The invention is described below with reference to the figures accompanying the present description.

FIGS. 1 to 4 show how the sampling method of the invention is implemented.

Figure 5:
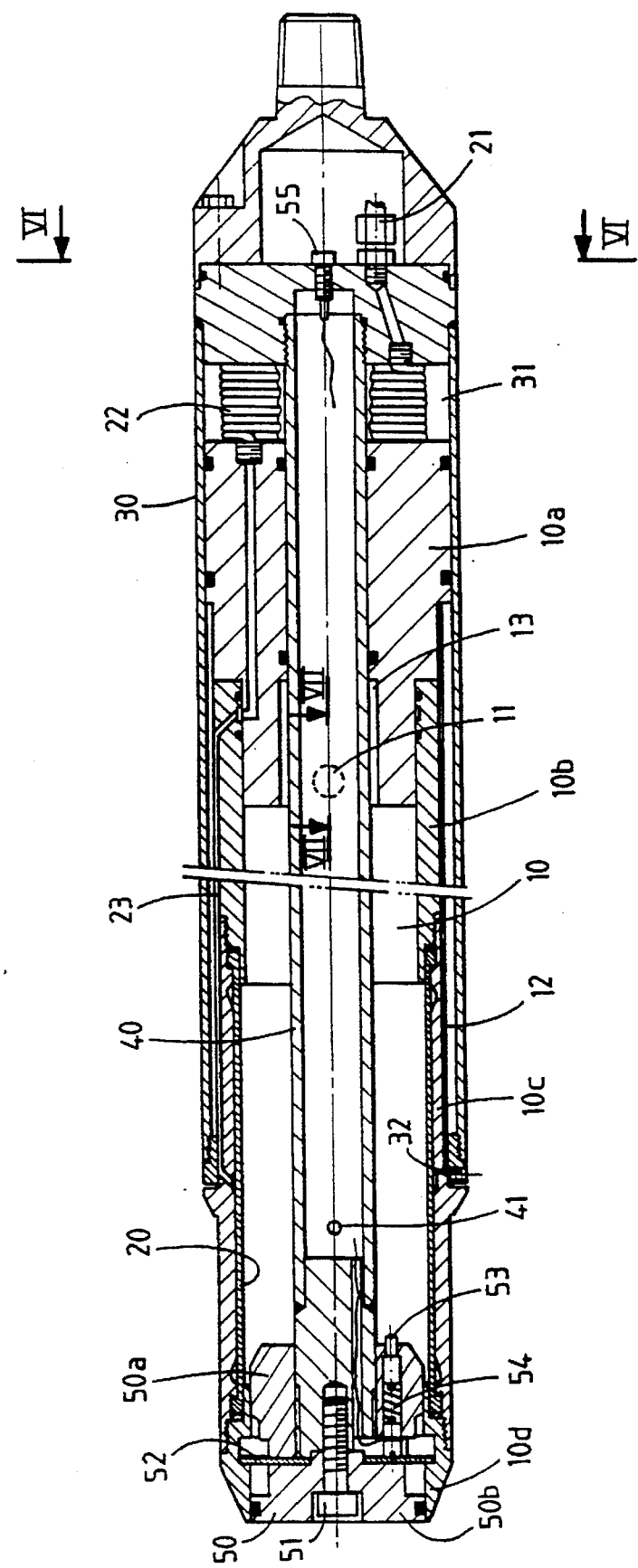
FIG. 5 is a vertical section on V—V of a sampling device constituting a preferred variant of the invention.
Figure 6:
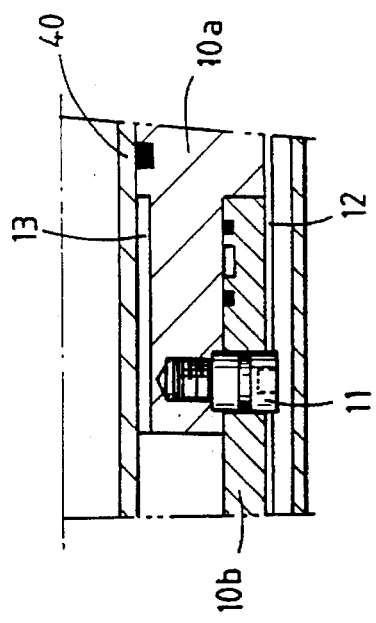
FIG. 6 is a plan view of said device of the invention in section on VI—VI.
Figure 7:
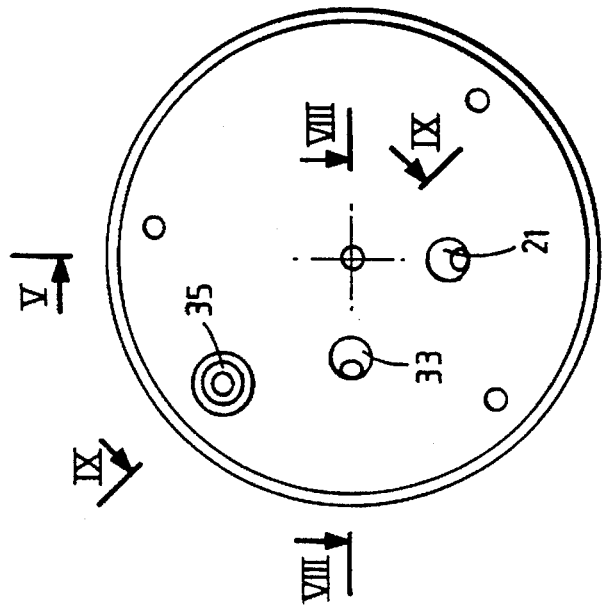
FIG. 7 is a view of said device in section on VI—VI.

In FIGS. 1 to 4, it can be seen that the device used essentially comprises a sampling cylinder 1 open at its bottom and provided in the vicinity of said bottom with an inflatable membrane 2 suitable, on inflation, for closing said bottom. Said sampling cylinder 1 is displaceable in translation inside an outer cylinder 3. In addition, it is guided during said translation by a central rod 4 that is secured at its bottom end to a stationary piston 5 and at its top end to the head of the outer cylinder 3.

Said device has a head constituted by a pressure chamber in which the sample-taking equipment or cylinder 1 moves in translation by air compression. The vent-forming means are not shown in said FIGS. 1 to 4.

Said device is used as follows:

As shown in FIG. 1, it is brought over the location from which the sample of material M is to be taken.

Initially it is positioned with its bottom beneath the surface level of the material M to be sampled. While the inflatable membrane 2 is retracted, the sampling cylinder 1 then dives into and fills with said material M. The bottom edge of the sampling cylinder 1 is chamfered to facilitate its penetration into said material M. The same applies to the bottom edge of said outer cylinder 3.

Once said sampling cylinder 1 is filled with said material M, said membrane 2 is inflated by being put under pressure using a suitable gas—e.g. nitrogen—so that it constitutes closure means for said sampling cylinder 1 as filled with a sample of said material M. Said closure means are constituted by an annular tube whose inner wall presses against itself.

In this way a determined quantity of said material M is enclosed in the inside volume of the sampling cylinder 1 (FIG. 2).

Sealing of said cylinder may be monitored by measuring the internal pressure of the annular tube.

Once the sample has been taken, the head is raised together with the full sampling cylinder in its low position, and it is then placed over a receptacle or pot 6 for storage or subsequent analysis of the sample of material (FIG. 3).

The shutter—the inflated membrane 2—is then retracted by applying suction to the inside of the annular tube.

The sample of material M then runs out both under gravity and under drive from the piston 5 due to the outer cylinder 3 being lowered over the sampling cylinder 1 which is in abutment against the receptacle or pot 6. As it comes down, the piston 5 scrapes the inside walls of said sampling cylinder 1, thereby "cleaning" them.

The device is then in the situation shown diagrammatically in FIG. 4.

FIGS. 5 to 9 show a preferred variant of the device of the invention in greater detail.

In this variant, the sampling cylinder 10 is not a single piece. It is made up of four portions referenced from top to bottom as follows: 10a, 10b, 10c, and 10d. Said portions 10b and 10c constitute the sampling equipment proper. The top portion 10a is a moving piston secured to said equipment 10b–10c by means of grub screw 11. The bottom portion 10d is a chamfered block which serves firstly to facilitate penetration of said sampling cylinder 10 into the material to be sampled, and secondly to co-operate in securing the bottom portion of the inflatable membrane 20.

The top portion of said inflatable membrane 20 is secured between 10b and 10c.

Said sampling cylinder 10 is caused to move in vertical translation inside the outer cylinder 30. During this translation movement, it is guided by the central rod 40. Said central rod 40 is hollow and its bottom end is secured by means of a screw 51 to a stationary piston 50.

Said stationary piston 50 includes a top portion 50a—a nut—and a bottom portion 50b—a clamping washer—that are secured to each other and that hold a gasket 52 between them. The gasket 52 is deformable. While the sampling cylinder 10 is moving downwards, it provides sealing between the cavity released for sampling and the pressure chamber 31 (by preventing the material from gaining access to the space between the top of the piston 50a and the bottom of the portion 10a). While the cylinder 30 is moving down over said cylinder 10, it cleans the inside walls thereof by scraping them.

The top portion 50a of said stationary piston 50 includes a moving electrical contact 53 mounted on a compression spring 54, said spring accommodating inaccuracies in the vertical positioning of the bottom portion of the moving piston 10a. Said contact 53 mounted in a housing that is insulated from ground serves to provide ground continuity on coming into contact with the base 55. Its purpose is to indicate that the sampling cylinder 10 is in its sampling position (its low position). Said position corresponds to said contact 53 coming into contact with the top portion 10a of the sampling cylinder 10. Movement of said cylinder 10 in translation inside the outer cylinder 30 is also guided by co-operation between means 12 and 32 situated respectively in the outside face of said cylinder 10 and the inside face of said cylinder 30. Said means 12 comprise a longitudinal groove; said means 32 comprise a stud fixed by a screw; said stud 32 slides along said longitudinal groove 12 during relative translation movement of one cylinder relative to the other. Said means prevent any rotation between said cylinders 10 and 30.

The inflatable membrane 20 is intended, on being inflated, to close the sampling cavity when the sampling cylinder 10 has been filled and is in its low position.

To this end, it is connected to a source that feeds it with fluid under pressure. The circuit for feeding said fluid comprises a coupling 21, a hose 22, and a capillary 23. Said hose 22 is wound helically the pressure chamber 31. It unwinds as the sampling cylinder 10 moves down to its low, sampling position.

Figure 8:
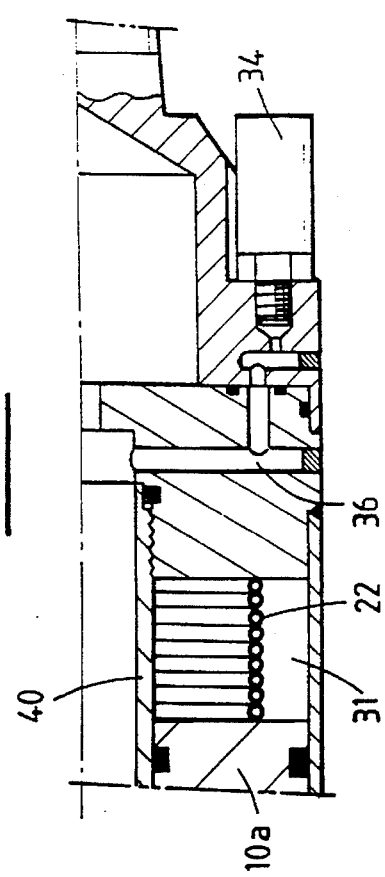
FIG. 8 is a (half) section view of said device on VIII—VIII.

To lower said sampling cylinder 10 into its sampling position, a fluid under pressure is caused to act inside the pressure chamber 31. Said fluid brought in from the outside via a duct 33 (FIG. 8). When the outer cylinder 30 is moved down over said sampling cylinder 10 in its low position, said fluid must be capable of being removed. To this end, use is again made of the duct 33 which must open out to a vent.

Figure 9:
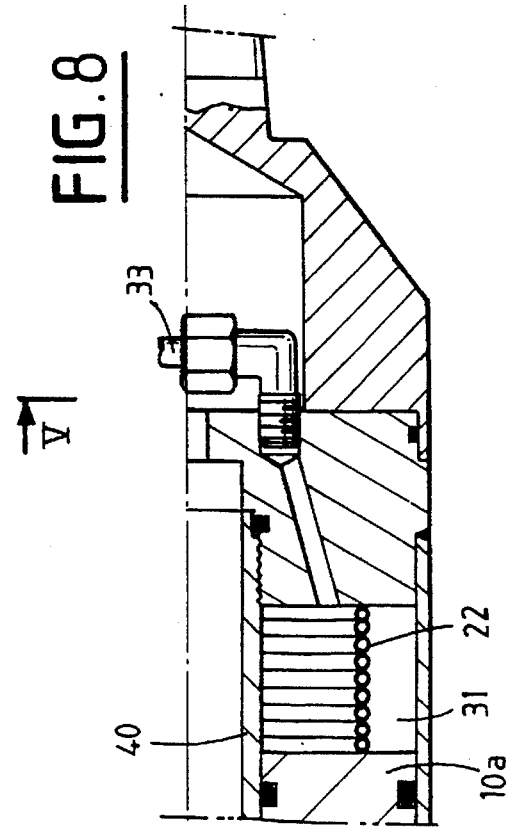
FIG. 9 is a (half) section view of said device on IX—IX.

As said sampling cylinder 10 is moving down into its sampling position, the air contained in the empty sampling cavity must be capable of escaping. To this end, two orifices 41 are formed in the bottom portion of the hollow central rod 40 in the vicinity of the top portion 50a of the piston 50, and the top portion of said hollow central rod 40 is connected to the outside. FIG. 9 shows that said air escapes to the outside via a vent 34.

Finally, said hollow rod 40 is advantageously used to improve the cleaning of the inside walls of the sampling cylinder 10 by scraping by means of the gasket 52 while the outer cylinder 30 is moving down over said sampling cylinder 10 which is then empty and in its low position. A cleaning liquid is injected under pressure at 34 (to this end an appropriate injection device shown mounted on the vent orifice). Said cleaning liquid travels along a rinsing circuit 36 which communicates with said rod 40. Said liquid leaves via 41 to penetrate into an annular gap 13 provided in the top portion 10a of the sampling cylinder 10. Under the pressure of said liquid and given the relative movement between the two cylinders, the gasket 52 no longer provides sealing and the cleaning liquid can be expelled downwards (the sampling cylinder 10 being in its low position).

The operation of the device of the invention is briefly described below with reference to FIGS. 5 to 9.

Said device is put into contact with the substance from which a sample is to be taken. The piston 50 is advantageously pushed into said substance, at least in part. Fluid under pressure is injected into the chamber 31 via 33. Under drive from said fluid, the sampling cylinder 10 moves downwards. Its downward travel is guided by the means 30, 40, 12, and 32. As it moves down, the air initially present in the sampling cavity escapes via 41, moves up along the hollow rod 40 and escapes to the outside via the vent 34. As soon as said sampling cylinder touches the contact 53, fluid feed is interrupted. Said cylinder is then in abutment against the stationary piston 50.

Once the cylinder is filled with the substance to be sampled, the membrane 20 is inflated by injecting a fluid under pressure via 21.

The device as a whole—sampling cylinder in its low position and full of substance—is then raised and put into position over a receptacle for the sampled substance (see FIG. 3).

The membrane is then deflated by being subjected to suction. The sampling cylinder thus discharges its contents. It is then to be found empty and in its low position with the outer cylinder 30 above it. Said outer cylinder 30 is then lowered over said empty cylinder 10. As it moves down, a cleaning fluid is injected under pressure via 34 (to this end, an appropriate injection device is mounted on the vent orifice). Said fluid circulates inside the hollow rod 40, escapes therefrom via 41, circulates in the annular groove 13 and escapes downwards by deformation of the gasket 52. It may be observed that said gasket 52 provides sealing while the sampling cylinder 10 is moving downwards, but it no longer does so when the outer cylinder 30 is moving downwards.

During said downward movement of said outer cylinder 30 over the cylinder 10 in its low position, the pressure in the chamber 31 is in excess. During this stage of the method, the coupling 33 opens out via a vent.

It is specified below by way of non-limiting illustration that a device of the invention, as shown in FIGS. 5 to 9, may provide an effective sampling volume of about 1 liter, and that it is entirely suitable for sampling sludges having viscosities lying in the range 1 centipoise to 120 poises (viscosities measured with a Brookfield LVT viscosity meter fitted with a No. 2 disk rotating at 60 rpm (1983 model)).

Its essential components are made of stainless steel. The stationary piston is made of bronze. The membrane constituting the inflatable shutter means is a rubber membrane obtained by molding. It is inflated under air or nitrogen pressure to a pressure lying in the range 1.2 bars to 2 bars. At such pressures, it is capable of retaining a liquid in liquid-tight manner.

To lower the sampling cylinder, compressed air or nitrogen is used. The outer cylinder is moved down over the sampling cylinder while in its low position under manual drive.

We claim:

1. A device for taking samples of a material comprising:

a hollow sampling cylinder having an outer wall defining a cavity therein and an open bottom communicating with said cavity;

an outer cylinder having a top portion and an open bottom, said sampling cylinder being mounted within said outer cylinder for movement relative thereto between a first position in which said sampling cylinder is received within said outer cylinder and a second position in which said sampling cylinder is displaced downwardly relative to said outer cylinder, said outer cylinder guiding said sampling cylinder during relative movement therebetween;

a rod having a top end and a bottom end and being connected at its top end to said outer cylinder, said rod cooperating with said outer cylinder to guide said sampling cylinder;

a stationary piston secured to said bottom end of said rod, said piston stopping and positioning said sampling cylinder in said second position;

said outer cylinder and said sampling cylinder defining therebetween a pressure chamber within which said sampling cylinder is displaced;

inflatable shutter means positioned near said open bottom of said sampling cylinder and moveable between an inflated position wherein said inflatable shutter means shuts said open bottom of said sampling cylinder after said cylinder has filled with said material thereby holding said material in said sampling cylinder, and a collapsed position wherein said inflatable shutter means does not close said open bottom of said sampling cylinder;

injecting means for injecting pressurized fluid into said pressure chamber for moving said sampling cylinder to said second position and for exhausting said pressurized fluid from said pressure chamber as said outer cylinder is moved downwardly over said sampling cylinder for returning said sampling cylinder to said first position;

venting means for exhausting a gas contained within said sampling cavity as said sampling cylinder moves from said first position to said second position;

said outer wall of said sampling cylinder having a conduit therein communicating at one end with said inflatable shutter means for transmitting pressurized fluid to said inflatable shutter means for movement thereof to said inflated position and for suctioning said pressurized fluid from said inflatable shutter means for movement thereof to said collapsed position; and a flexible hose in said pressure chamber connected at one end to a source of pressurized fluid and at the other end to said conduit for feeding pressurized fluid from said source to said inflatable shutter means.

2. A sampling device according to claim 1 wherein an outside face of said sampling cylinder and an inside face of said outer cylinder include, over at least a portion of their heights, complementary cooperating means for preventing said cylinders from rotating relative to each other.

3. A sampling device according to claim 1, wherein said piston includes an electrical contact on its top face for indicating that said sampling cylinder is in said second position.

4. A sampling device according to claim 1, wherein said piston comprises two united portions having a gasket therebetween, said gasket serving firstly as a seal between said sampling cavity and said pressure chamber during movement of said sampling cylinder to its second position and secondly as a scraper during downwards movement of said outer cylinder over said sampling cylinder as said sampling cylinder returns to its first position.

5. A sampling device according to claim 4, wherein said rod is hollow and connected at its top end to a liquid injector device for injecting a cleaning liquid through said rod into the empty sampling cylinder during the downward movement of said outer cylinder thereon, said liquid passing out through at least one orifice in said rod into an annular gap formed in the top portion of said sampling cylinder, said cylinder being in said second position and said liquid escaping during downward movement of said outer cylinder by virtue of the resilience of said gasket held between said two portions of said piston.

6. A sampling device according to claim 1, wherein the bottom end of said sampling cylinder is configured to penetrate into the material to be sampled.

7. A sampling device according to claim 1, wherein said rod is hollow for defining an axial bore therein and has at least one orifice communicating said bore with said sampling cavity, and wherein said venting means communicates with the upper end of the axial bore, thereby providing a fluid path between said sampling cavity and said venting means.

8. A sampling device according to claim 7, further comprising:

a liquid feed source connected to said venting means for injecting a cleaning liquid into said sampling cavity through said orifice.

9. The sampling device according to claim 1, wherein said pressure chamber is defined at its lower end by said stationary piston as said sampling cylinder moves to its second position.

10. The sampling device according to claim 9, wherein said stationary piston includes a gasket abutting the inside wall of the sampling cylinder for sealing the sampling cavity from the pressure chamber.

11. A sampling device according to claim 1, wherein said inflatable shutter means comprises a rubber membrane.

12. A sampling device according to claim 1, wherein said flexible hose is helically wound about said rod.

13. A sampling device according to claim 1, further comprising:

a liquid feed source connected to said venting means for injecting a cleaning liquid into said sampling cavity.

14. A sampling device according to claim 1, wherein said rod is located centrally within said outer cylinder.

15. A sampling device according to claim 6, wherein said bottom end of said sampling device is chamfered.

16. A sampling device according to claim 1, wherein said stationary piston includes a circumferential sealing ring dimensioned for close contact with the inside wall of the sampling cylinder at the bottom thereof below said inflatable shutter means for closing the bottom of the sampling device when the sampling cylinder is in its first position, and a gasket above said sealing ring having an outer diameter greater than the outer diameter of the sealing ring for close contact with the inflatable shutter means and the upper portion of the inside wall of the sampling cavity during relative movement of the sampling cylinder and outer cylinder, whereby said gasket seals the pressure chamber from the sampling cavity during downward movement of the sampling cavity to its second position and scrapes the inside wall of the sampling cylinder for cleaning same as said outer cylinder is moved downwardly over said sampling cylinder for returning said sampling cylinder to said first position.

17. A device for taking samples of a material comprising:

a hollow sampling cylinder having an outer wall defining a cavity therein and an open bottom communicating with said cavity;

an outer cylinder having a top portion and an open bottom, said sampling cylinder being mounted within said outer cylinder for movement relative thereto between a first position in which said sampling cylinder is received within said outer cylinder and a second position in which said sampling cylinder is displaced downwardly relative to said outer cylinder, said outer cylinder guiding said sampling cylinder during relative movement therebetween;

a rod having a top end and a bottom end and being connected at its top end to said outer cylinder, said rod cooperating with said outer cylinder to guide said sampling cylinder;

said outer cylinder and said sampling cylinder defining therebetween a pressure chamber within which said sampling cylinder is displaced;

inflatable shutter means positioned near said open bottom of said sampling cylinder and moveable between an inflated position wherein said inflatable shutter means shuts said open bottom of said sampling cylinder after said cylinder has filled with said material thereby holding said material in said sampling cylinder, and a collapsed position wherein said inflatable shutter means does not close said open bottom of said sampling cylinder;

a stationary piston secured to said bottom end of said rod, said stationary piston including a circumferential sealing ring dimensioned for close contact with the inside wall of the sampling cylinder at the bottom thereof below said inflatable shutter means for closing the bottom of the sampling device when the sampling cylinder is in its first position, and a gasket above said sealing ring and having an outer diameter greater than the outer diameter of the sealing ring for close contact with the inflatable shutter means and an upper portion of an inside wall of the sampling cavity during relative movement of the sampling cylinder and outer cylinder, whereby the gasket seals the pressure chamber from the sampling cavity during downward movement of the sampling cylinder to its second position and scrapes the inside wall of the sampling cylinder for cleaning same as said outer cylinder is moved downwardly over said sampling cylinder for returning said sampling cylinder to its first position, said piston stopping and positioning said sampling cylinder in said second position;

injecting means for injecting pressurized fluid into said pressure chamber for moving said sampling cylinder to said second position and for exhausting said pressurized fluid from said pressure chamber as said outer cylinder is moved downwardly over said sampling cylinder for returning said sampling cylinder to said first position;

venting means for exhausting a gas contained within said sampling cavity as said sampling cylinder moves from said first position to said second position;

said outer wall of said sampling cylinder having a conduit therein communicating at one end with said inflatable shutter means for transmitting pressurized fluid to said inflatable shutter means for movement thereof to said inflated position and for suctioning said pressurized fluid from said inflatable shutter means for movement thereof to said collapsed position; and a flexible hose in the pressure chamber connected at one end to a source of pressurized fluid and at the other end to said conduit for feeding pressurized fluid from said source to said inflatable shutter means.

18. A device for taking samples of a material comprising:

a hollow sampling cylinder having an outer wall defining a cavity therein and an open bottom communicating with said cavity;

an outer cylinder having a top portion and an open bottom, said sampling cylinder being mounted within said outer cylinder for movement relative thereto between a first position in which said sampling cylinder is received within said outer cylinder and a second position in which said sampling cylinder is displaced downwardly relative to said outer cylinder, said outer cylinder guiding said sampling cylinder during relative movement therebetween;

venting means for exhausting a gas contained within said sampling cavity as said sampling cylinder moves from said first position to said second position;

a hollow rod having a top end and a bottom end and being connected at its top end to said outer cylinder, said rod cooperating with said outer cylinder to guide said sampling cylinder during relative movement between said sampling cylinder and said outer cylinder, said rod defining an axial bore therein and having at least one orifice communicating said bore with said sampling cavity, and wherein said venting means communicates with the upper end of the axial bore, thereby providing a fluid path between said sampling cavity and said venting means, said upper end of said axial bore also being connected to a liquid injector device for injecting a cleaning liquid into the empty sampling cylinder through said orifice when said sampling cylinder is in said second position and during downward movement of said outer cylinder thereon, said liquid filling an annular gap formed between a top portion of said sampling cylinder and said rod;

said outer cylinder and said sampling cylinder defining therebetween a pressure chamber within which said sampling cylinder is displaced;

inflatable shutter means positioned near said open bottom of said sampling cylinder and moveable between an inflated position wherein said inflatable shutter means shuts said open bottom of said sampling cylinder after said cylinder has filled with said material thereby holding said material in said sampling cylinder, and a collapsed position wherein said inflatable shutter means does not close said open bottom of said sampling cylinder;

a stationary piston secured to said bottom end of said rod, said stationary piston including a circumferential sealing ring dimensioned for close contact with the inside wall of the sampling cylinder at the bottom thereof below said inflatable shutter means for closing the bottom of the sampling device when the sampling cylinder is in its first position, and a gasket above said sealing ring and having an outer diameter greater than the outer diameter of the sealing ring for close contact with the inflatable shutter means and an upper portion of an inside wall of the sampling cavity during relative movement of the sampling cylinder and outer cylinder, whereby the gasket seals the pressure chamber from the sampling cavity during downward movement of the sampling cylinder to its second position and scrapes the inside wall of the sampling cylinder for cleaning same as said outer cylinder is moved downwardly over said sampling cylinder for returning said sampling cylinder to its first position, said piston stopping and positioning said sampling cylinder in said second position;

injecting means for injecting pressurized fluid into said pressure chamber for moving said sampling cylinder to said second position and for exhausting said pressurized fluid from said pressure chamber as said outer cylinder is moved downwardly over said sampling cylinder for returning said sampling cylinder to said first position;

said outer wall of said sampling cylinder having a conduit therein communicating at one end with said inflatable shutter means for transmitting pressurized fluid to said inflatable shutter means for movement thereof to said inflated position and for suctioning said pressurized fluid from said inflatable shutter means for movement thereof to said collapsed position; and a flexible hose in the pressure chamber connected at one end to a source of pressurized fluid and at the other end to said conduit for feeding pressurized fluid from said source to said inflatable shutter means.

* * * * *